Jan. 7, 1947. M. BAZZANELLA Plant Pat. 722
APPLE TREE
Filed Oct. 8, 1945
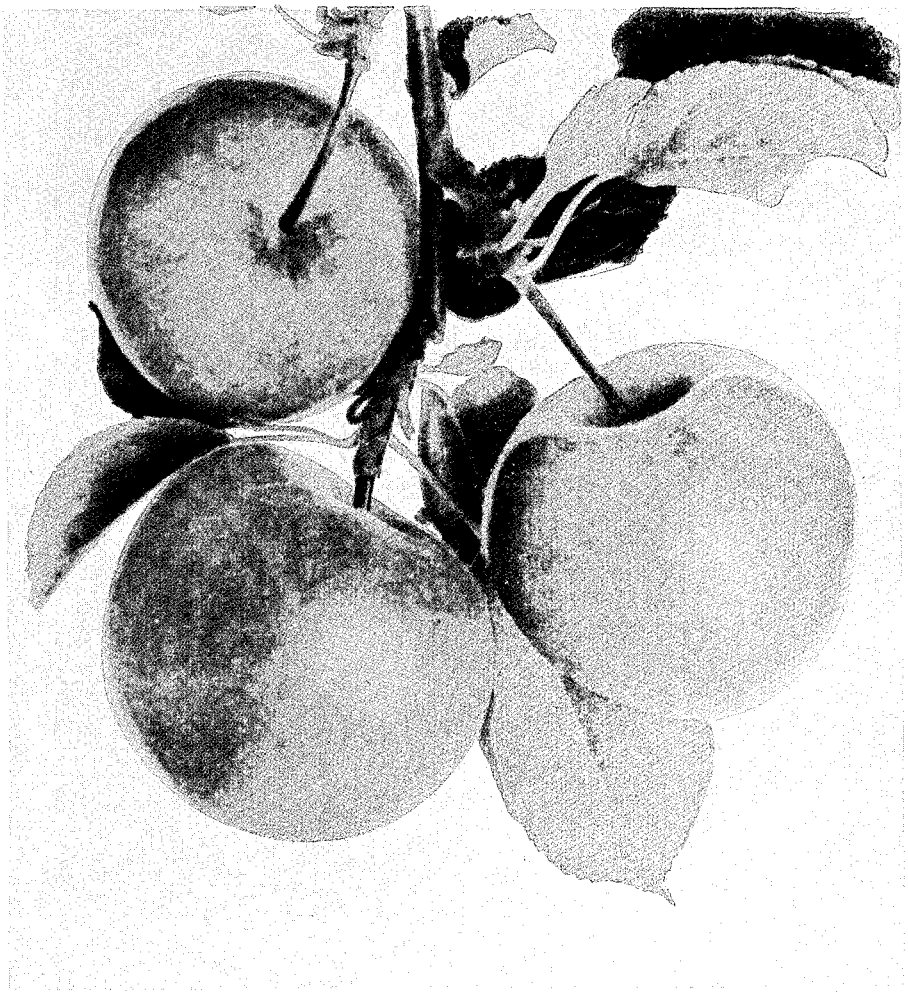
Mat Bazzanella,
By John C. Daul,
Attorney.

Patented Jan. 7, 1947

Plant Pat. 722

UNITED STATES PATENT OFFICE

722

APPLE TREE

Max Bazzanella, Mineral, Va.

Application October 8, 1945, Serial No. 620,996

1 Claim. (Cl. 47—62)

The invention relates to a new and distinct variety of apple tree which remains dormant and blooms thirty days later than the Winesap. The fruit ripens about the same time as the Winesap.

The tree is hardy and pest-resistant, medium size, upright, and spreading; trunk, medium, smooth; leaves, large, thick, rugose, light green; blooms on or about the 18th of May; flowers, medium size, white; fertile productive, regular bearer; fruit, roundish, medium size; stem, short, dark bronze color; tough skin; flesh, white, firm; core, small, closed seeds; medium sub-acid spicy, quince-like flavor; good for drying and general home use.

The drawing shows a branch with the disposition of the fruit thereon.

This new variety has been asexually reproduced and its characteristics found to be fixed.

This apple tree has been originated from a seed by Max Bazzanella and is located on his farm in Louisa County, Virginia. It has borne regularly every year for the past 10 years. The tree is about 15 years old. Budding has occurred from it on several occasions which have been set out in different fields and all those that have been budded have come true just the same as the original tree, and they stay dormant just the same.

Having now fully described my invention, what I claim as new and desire to secure by Letters Patent is:

A new and distinct variety of apple tree substantially as herein disclosed, characterized by its quality of remaining dormant about thirty days longer and blooming thirty days later than the Winesap; its upright and spreading habit, pest resistance, and hardy productive flowers; its fruit of dark bronze color, with tough skin, hard flesh, quince-like flavor, good drying and keeping qualities.

MAX BAZZANELLA.